(12) United States Patent  (10) Patent No.: US 9,339,229 B2
Bernstein  (45) Date of Patent: May 17, 2016

(54) ANALYTE MONITORING DEVICES AND METHODS

(75) Inventor: Daniel M. Bernstein, El Granada, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 483 days.

(21) Appl. No.: 13/877,543

(22) PCT Filed: Dec. 13, 2011

(86) PCT No.: PCT/US2011/064584
§ 371 (c)(1),
(2), (4) Date: May 9, 2013

(87) PCT Pub. No.: WO2012/145027
PCT Pub. Date: Oct. 26, 2012

(65) Prior Publication Data
US 2014/0148665 A1     May 29, 2014

Related U.S. Application Data

(60) Provisional application No. 61/477,489, filed on Apr. 20, 2011.

(51) Int. Cl.
*A61B 5/00*     (2006.01)
*A61B 5/145*    (2006.01)
*A61B 5/1473*   (2006.01)

(52) U.S. Cl.
CPC ............. *A61B 5/6833* (2013.01); *A61B 5/1473* (2013.01); *A61B 5/14532* (2013.01); *A61B 5/14546* (2013.01); *A61B 2560/0252* (2013.01)

(58) Field of Classification Search
CPC .................................................. A61B 5/14532
See application file for complete search history.

(56) References Cited

U.S. PATENT DOCUMENTS

| 4,545,382 A | 10/1985 | Higgins et al. |
| 4,711,245 A | 12/1987 | Higgins et al. |
| 5,262,035 A | 11/1993 | Gregg et al. |
| 5,262,305 A | 11/1993 | Heller et al. |
| 5,264,104 A | 11/1993 | Gregg et al. |

(Continued)

FOREIGN PATENT DOCUMENTS

| WO | 03/077970 | 9/2003 |
| WO | 2009/059194 | 5/2009 |
| WO | 2011/025549 | 3/2011 |

*Primary Examiner* — Christian Jang
(74) *Attorney, Agent, or Firm* — Edward J. Baba; Bozicevic, Field & Francis LLP

(57) ABSTRACT

On-body units are provided and include a transcutaneous analyte sensor, electronic circuitry electrically coupled to the sensor, and an on-body housing having electrical contacts disposed thereon. The on-body housing comprises a substantially flat surface and a curved and convex surface opposite the substantially flat surface. Systems and methods including the on-body units are also provided. Methods for performing continuity measurements using on-body units are also provided. The methods include positioning an on-body unit (OBU) on a skin of a subject, contacting a continuity test instrument to the OBU; and performing a continuity measurement with the continuity test instrument. An AC signal may be provided across two electrical contacts, or a DC signal may be provided across two electrical contacts in opposite directions for the same amount of time. The measurement may be performed with one electrical contact, or with isolated electrical contacts.

28 Claims, 7 Drawing Sheets

(56) References Cited

U.S. PATENT DOCUMENTS

| | | |
|---|---|---|
| 5,320,725 A | 6/1994 | Gregg et al. |
| 5,356,786 A | 10/1994 | Heller et al. |
| 5,509,410 A | 4/1996 | Hill et al. |
| 5,593,852 A | 1/1997 | Heller et al. |
| 5,601,435 A | 2/1997 | Quy |
| 5,628,890 A | 5/1997 | Carter et al. |
| 5,711,607 A | 1/1998 | Bernstein |
| 5,820,551 A | 10/1998 | Hill et al. |
| 5,822,715 A | 10/1998 | Worthington et al. |
| 5,899,855 A | 5/1999 | Brown |
| 5,918,603 A | 7/1999 | Brown |
| 6,071,391 A | 6/2000 | Gotoh et al. |
| 6,120,676 A | 9/2000 | Heller et al. |
| 6,121,009 A | 9/2000 | Heller et al. |
| 6,143,164 A | 11/2000 | Heller et al. |
| 6,144,837 A | 11/2000 | Quy |
| 6,161,095 A | 12/2000 | Brown |
| 6,175,752 B1 | 1/2001 | Say et al. |
| 6,270,455 B1 | 8/2001 | Brown |
| 6,284,478 B1 | 9/2001 | Heller et al. |
| 6,299,757 B1 | 10/2001 | Feldman et al. |
| 6,338,790 B1 | 1/2002 | Feldman et al. |
| 6,377,894 B1 | 4/2002 | Deweese et al. |
| 6,461,496 B1 | 10/2002 | Feldman et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,540,891 B1 | 4/2003 | Stewart et al. |
| 6,560,471 B1 | 5/2003 | Heller et al. |
| 6,591,125 B1 | 7/2003 | Buse et al. |
| 6,592,745 B1 | 7/2003 | Feldman et al. |
| 6,600,997 B2 | 7/2003 | Deweese et al. |
| 6,616,819 B1 | 9/2003 | Liamos et al. |
| 6,618,934 B1 | 9/2003 | Feldman et al. |
| 6,676,816 B2 | 1/2004 | Mao et al. |
| 6,730,200 B1 | 5/2004 | Stewart et al. |
| 6,736,957 B1 | 5/2004 | Forrow et al. |
| 6,746,582 B2 | 6/2004 | Heller et al. |
| 6,749,740 B2 | 6/2004 | Liamos et al. |
| 6,764,581 B1 | 7/2004 | Forrow et al. |
| 6,773,671 B1 | 8/2004 | Lewis et al. |
| 6,881,551 B2 | 4/2005 | Heller et al. |
| 6,893,545 B2 | 5/2005 | Gotoh et al. |
| 6,942,518 B2 | 9/2005 | Liamos et al. |
| 7,041,468 B2 | 5/2006 | Drucker et al. |
| 7,167,818 B2 | 1/2007 | Brown |
| 7,299,082 B2 | 11/2007 | Feldman et al. |
| 2004/0186365 A1 | 9/2004 | Jin et al. |
| 2006/0025662 A1 | 2/2006 | Buse et al. |
| 2006/0091006 A1 | 5/2006 | Wang et al. |
| 2007/0068807 A1 | 3/2007 | Feldman et al. |
| 2007/0095661 A1 | 5/2007 | Wang et al. |
| 2007/0108048 A1 | 5/2007 | Wang et al. |
| 2007/0199818 A1 | 8/2007 | Petyt et al. |
| 2008/0066305 A1 | 3/2008 | Wang et al. |
| 2008/0102441 A1 | 5/2008 | Chen et al. |
| 2008/0148873 A1 | 6/2008 | Wang |
| 2008/0267823 A1 | 10/2008 | Wang et al. |
| 2009/0120810 A1 | 5/2009 | Phan et al. |
| 2009/0143761 A1 | 6/2009 | Cantor et al. |
| 2010/0076293 A1 | 3/2010 | Bernstein et al. |
| 2010/0198034 A1 | 8/2010 | Thomas et al. |
| 2010/0213057 A1 | 8/2010 | Feldman et al. |
| 2010/0324392 A1 | 12/2010 | Yee et al. |
| 2010/0325868 A1 | 12/2010 | Wang et al. |
| 2010/0326842 A1 | 12/2010 | Mazza et al. |
| 2011/0077490 A1* | 3/2011 | Simpson ............ A61B 5/14532 600/345 |
| 2011/0079522 A1 | 4/2011 | Webster et al. |

* cited by examiner

ANALYTE MONITORING DEVICES AND METHODS

CROSS-REFERENCE TO RELATED APPLICATIONS

Pursuant to 35 U.S.C. §119(e), this application claims priority to U.S. Provisional Patent Application No. 61/477,489 filed on Apr. 20, 2011, the disclosure of which is herein incorporated by reference in its entirety.

This application is also related to U.S. patent application Ser. No. 12/393,921, filed Feb. 26, 2009; U.S. patent application Ser. No. 12/807,278, filed Aug. 31, 2010; U.S. patent application Ser. No. 12/876,840, filed Sep. 7, 2010; U.S. Provisional Application No. 61/325,155, filed Apr. 16, 2010; U.S. Provisional Application No. 61/325,260, filed Apr. 16, 2010; U.S. Provisional Application No. 61/247,519, filed Sep. 30, 2009; U.S. Provisional Application No. 61/415,174, filed Nov. 18, 2010; and U.S. Provisional Application No. 61/422,490, filed Dec. 13, 2010. The disclosures of the above-mentioned applications are incorporated herein by reference in their entirety.

BACKGROUND

Diabetes Mellitus is an incurable chronic disease in which the body does not produce or properly utilize insulin. Insulin is a hormone produced by the pancreas that regulates blood glucose. In particular, when blood glucose levels rise, e.g., after a meal, insulin lowers the blood glucose levels by facilitating blood glucose to move from the blood into the body cells. Thus, when the pancreas does not produce sufficient insulin (a condition known as Type 1 Diabetes) or does not properly utilize insulin (a condition known as Type II Diabetes), the blood glucose remains in the blood resulting in hyperglycemia or abnormally high blood sugar levels.

People suffering from diabetes often experience long-term complications. Some of these complications include blindness, kidney failure, and nerve damage. Additionally, diabetes is a factor in accelerating cardiovascular diseases such as atherosclerosis (hardening of the arteries), which often leads stroke, coronary heart disease, and other diseases, which can be life threatening.

The severity of the complications caused by both persistent high glucose levels and blood glucose level fluctuations has provided the impetus to develop diabetes management systems and treatment plans. In this regard, diabetes management plans historically included multiple daily testing of blood glucose levels typically by a finger-stick to draw and test blood. The disadvantage with finger-stick management of diabetes is that the user becomes aware of his blood glucose level only when he performs the finger-stick. Thus, blood glucose trends and blood glucose snapshots over a period of time is generally unknown. More recently, diabetes management has included the implementation of glucose monitoring systems. Glucose monitoring systems have the capability to monitor a user's blood glucose levels over a duration of time. Thus, such systems have the ability to illustrate not only present blood glucose levels but a snapshot of blood glucose levels and blood glucose fluctuations over a period of time.

SUMMARY

Aspects of the present disclosure relate to analyte monitoring systems, devices, and methods thereof. On-body units are provided and include a transcutaneous analyte sensor, electronic circuitry electrically coupled to the analyte sensor, and an on-body housing having electrical contacts disposed thereon. The on-body housing comprises a substantially flat surface and a curved and convex surface opposite the substantially flat surface. Systems and methods including the on-body units are also provided.

Aspects of the present disclosure relate to methods for performing continuity measurements on on-body units. The methods include positioning an on-body unit (OBU) on a skin of a subject, contacting a continuity test instrument to the OBU; and performing a continuity measurement with the continuity test instrument.

In certain embodiments, the methods include providing an alternating current signal to two of the electrical contacts on the on-body housing of the on-body units. In certain embodiments, the methods include providing a direct current signal in one direction across two of the electrical contacts for a specific amount of time, and then providing the direct current signal in the opposite direction across the same two electrical contacts for the same amount of time. In certain embodiments, the methods include performing a continuity measurement on one of the electrical contacts on the on-body housing. In certain embodiments, the methods include performing a continuity measurement across isolated electrical contacts on the on-body housing.

INCORPORATION BY REFERENCE

The following patents, applications and/or publications are incorporated herein by reference for all purposes: U.S. Pat. No. 7,041,468; U.S. Pat. No. 5,356,786; U.S. Pat. No. 6,175,752; U.S. Pat. No. 6,560,471; U.S. Pat. No. 5,262,035; U.S. Pat. No. 6,881,551; U.S. Pat. No. 6,121,009; U.S. Pat. No. 7,167,818; U.S. Pat. No. 6,270,455; U.S. Pat. No. 6,161,095; U.S. Pat. No. 5,918,603; U.S. Pat. No. 6,144,837; U.S. Pat. No. 5,601,435; U.S. Pat. No. 5,822,715; U.S. Pat. No. 5,899,855; U.S. Pat. No. 6,071,391; U.S. Pat. No. 6,120,676; U.S. Pat. No. 6,143,164; U.S. Pat. No. 6,299,757; U.S. Pat. No. 6,338,790; U.S. Pat. No. 6,377,894; U.S. Pat. No. 6,600,997; U.S. Pat. No. 6,773,671; U.S. Pat. No. 6,514,460; U.S. Pat. No. 6,592,745; U.S. Pat. No. 5,628,890; U.S. Pat. No. 5,820,551; U.S. Pat. No. 6,736,957; U.S. Pat. No. 4,545,382; U.S. Pat. No. 4,711,245; U.S. Pat. No. 5,509,410; U.S. Pat. No. 6,540,891; U.S. Pat. No. 6,730,200; U.S. Pat. No. 6,764,581; U.S. Pat. No. 6,299,757; U.S. Pat. No. 6,461,496; U.S. Pat. No. 6,503,381; U.S. Pat. No. 6,591,125; U.S. Pat. No. 6,616,819; U.S. Pat. No. 6,618,934; U.S. Pat. No. 6,676,816; U.S. Pat. No. 6,749,740; U.S. Pat. No. 6,893,545; U.S. Pat. No. 6,942,518; U.S. Pat. No. 6,514,718; U.S. Pat. No. 5,264,014; U.S. Pat. No. 5,262,305; U.S. Pat. No. 5,320,715; U.S. Pat. No. 5,593,852; U.S. Pat. No. 6,746,582; U.S. Pat. No. 6,284,478; U.S. Pat. No. 7,299,082; U.S. Patent Application No. 61/149,639, entitled "Compact On-Body Physiological Monitoring Device and Methods Thereof", U.S. patent application Ser. No. 11/461,725, filed Aug. 1, 2006, entitled "Analyte Sensors and Methods"; U.S. patent application Ser. No. 12/495,709, filed Jun. 30, 2009, entitled "Extruded Electrode Structures and Methods of Using Same"; U.S. patent application Ser. No. 12/698,124, filed Feb. 1, 2010, entitled "Compact On-Body Physiological Monitoring Devices and Methods Thereof"; U.S. patent application Ser. No. 12/698,129, filed Feb. 1, 2010, entitled "Analyte Sensor And Apparatus For Insertion Of The Sensor"; U.S. Patent Application Publication No. US2004/0186365; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No.

2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; US patent Application Publication No. 2010/0198034; U.S. Patent Application Publication No. 2010/0325868; and U.S. provisional application No. 61/149,639 titled "Compact On-Body Physiological Monitoring Device and Methods Thereof", the disclosures of each of which are incorporated herein by reference in their entirety.

DETAILED DESCRIPTION

Figure 2:
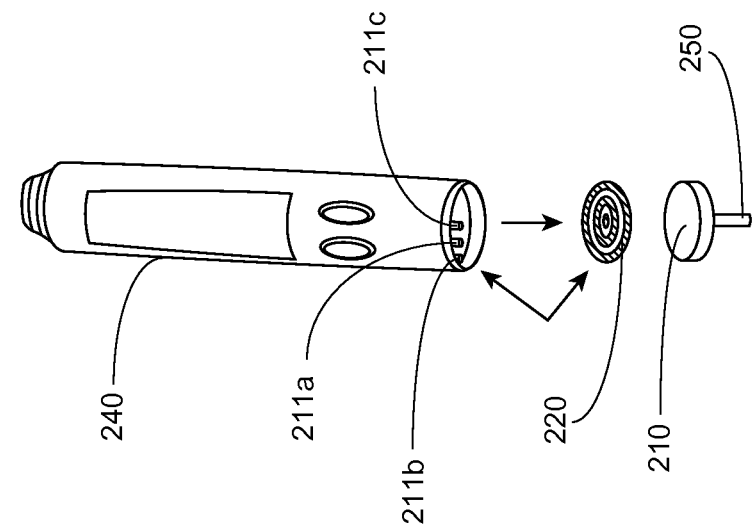
FIG. 2 illustrates the components of an analyte monitoring system, according to certain embodiments.

Before the present disclosure is described in additional detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

As summarized, aspects of the present disclosure relate to analyte monitoring systems, devices, and methods thereof. On-body units are provided and include a transcutaneous analyte sensor, electronic circuitry electrically coupled to the analyte sensor, and an on-body housing having electrical contacts disposed thereon. The on-body housing comprises a substantially flat surface and a curved and convex surface opposite the substantially flat surface. Systems and methods including the on-body units are also provided.

As summarized above, aspects of the present disclosure relate to methods for performing continuity measurements on on-body units. The methods include positioning an on-body unit (OBU) on a skin of a subject, contacting a continuity test instrument to the OBU; and performing a continuity measurement with the continuity test instrument. In certain embodiments, the methods include providing an alternating current signal to two of the electrical contacts on the on-body housing of the on-body units. In certain embodiments, the methods include providing a direct current signal in one direction across two of the electrical contacts for a specific amount of time, and then providing the direct current signal in the opposite direction across the same two electrical contacts for the same amount of time. In certain embodiments, the methods include performing a continuity measurement on one of the electrical contacts on the on-body housing. In certain embodiments, the methods include performing a continuity measurement across isolated electrical contacts on the on-body housing.

Systems

Aspects of the present disclosure relate to a transcutaneously positionable analyte sensor in signal communication with electronics which process signals from the analyte sensor transfer or otherwise provide the processed signals related to monitored analyte level to a receiver unit, a blood glucose meter or other devices configured to receive, process, analyze, output, display and/or store the processed signals. For example, analyte monitoring systems may include in vivo analyte sensors in fluid contact with body fluid such as interstitial fluid to monitor one or more analyte levels, such as glucose or a ketone body. Embodiments may include electronics and/or data processing, storage and/or communication components that are electrically coupled to the analyte sensor, and may include a housing that is placed or positioned on the body surface such as on the skin surface and adhered thereon with an adhesive and retained and maintained in the adhered position for the duration of the analyte monitoring time period using the analyte sensor such as, for example, about 15 days or more, about 10 days or more, about 7 days or more, or about 5 days or more, or about 3 days or more. The housing including the electronics and/or data processing, storage and/or data communication components may be positioned on discrete on-body locations including under clothing during the duration of the monitoring time period.

The analyte monitoring device that is coupled to the body and includes the analyte sensor, housing, and electronic circuitry is also referred to herein as an "on-body unit", "OBU", "on body patch", and "patch". In some instances, the analyte monitoring device as a whole may collectively be referred to as a "sensor" or "analyte sensor" or "self-powered sensor".

In some embodiments, the housing of the on body patch or housing of the electronics is water proof such that the user or the patient wearing the housing on a discrete on-body location may swim, shower, exercise or otherwise engage in daily activities with comfort and without inconvenience. Certain embodiments include the adhesive provided on the bottom surface of the housing in contact with the skin surface that retains the housing in position on the skin surface during the duration of the analyte monitoring time period discussed above. The on-body housing may be made from any variety of materials, including metals, metal alloys, polymers (e.g., plastics, rubber, etc.), combination thereof, etc.

In some aspects of the present disclosure, the OBU includes electrical contacts on the surface of the housing that includes the electronics and/or data processing, storage and/or communication components which are electrically coupled to the analyte sensor. When electrical contacts or probes provided on a reader unit is in physical contact with the corresponding electrical contacts on the surface of the housing that includes the electronics and/or data processing, storage and/or communication components, signals associated with the monitored analyte level by the OBU are acquired by the reader. The reader unit may also be referred to herein as "receiver unit". As described above, the reader unit may be an analyte monitoring device that is brought in contact with the OBU to acquire readings from the OBU. The reader may be, for example, an analyte meter (e.g., blood glucose meter), a mobile device that has been adapted to receive readings from the OBU, etc. Additional details regarding analyte data acquisition by physically contacting or touching the housing of sensor electronics with a reader (e.g., blood glucose meter) is provided in U.S. Provisional Application No. 61/247,519, the disclosure of which is incorporated herein by reference for all purposes. In this manner, embodiments of the present disclosure include analyte data acquisition or ability to obtain real time glucose data by physically touching or contacting the reader unit to the housing of the electronics and/or data processing, storage and/or communication components.

In some aspects of the present disclosure, the OBU is self-powered such that an external power source such as a battery is unnecessary to have the OBU generate a signal that is proportional to the monitored analyte concentration. In some instances, the OBU may include one or more power sources such as a battery, but is self-powered to the extent that a chemical reaction from the in-vivo analyte sensor provides necessary current to the electronics of the OBU for proper operation. The self-powered OBU may also be referred to herein generally as a "self-powered sensor". Additional details of self-powered sensors are provided in U.S. patent application Ser. No. 12/393,921 filed Feb. 26, 2009, the disclosure of which is incorporated herein by reference for all purposes. The absence of the external power source such as a battery (or the reduction in size of the external power source required) provides embodiments of the present disclosure with the size and/or the form factor of the housing for the electronics and/or data processing, storage and/or communication components to be small (for example, approximately the size of a dime—about 18 mm in diameter) that is comfortable to wear on the skin surface during the approximately 10 days of wear on the skin surface.

In some aspects of the present disclosure, real time analyte data acquisition is provided by physical contact between the reader unit and the housing of the OBU. Signals are provided to the reader unit that are associated with the real time analyte concentration (such as the real time glucose value) and/or monitored analyte concentration trend information for a predetermined time period (such as for example, the past 3 hours of glucose concentration that are monitored by the analyte sensor and stored by the electronics and/or data processing, storage and/or communication components in the housing). In some aspects, trend information may be stored and/or provided with the real time monitored analyte concentration where the predetermined time period may be about 1 hour, about 2 hours, about 5 hours or more.

Figure 1:
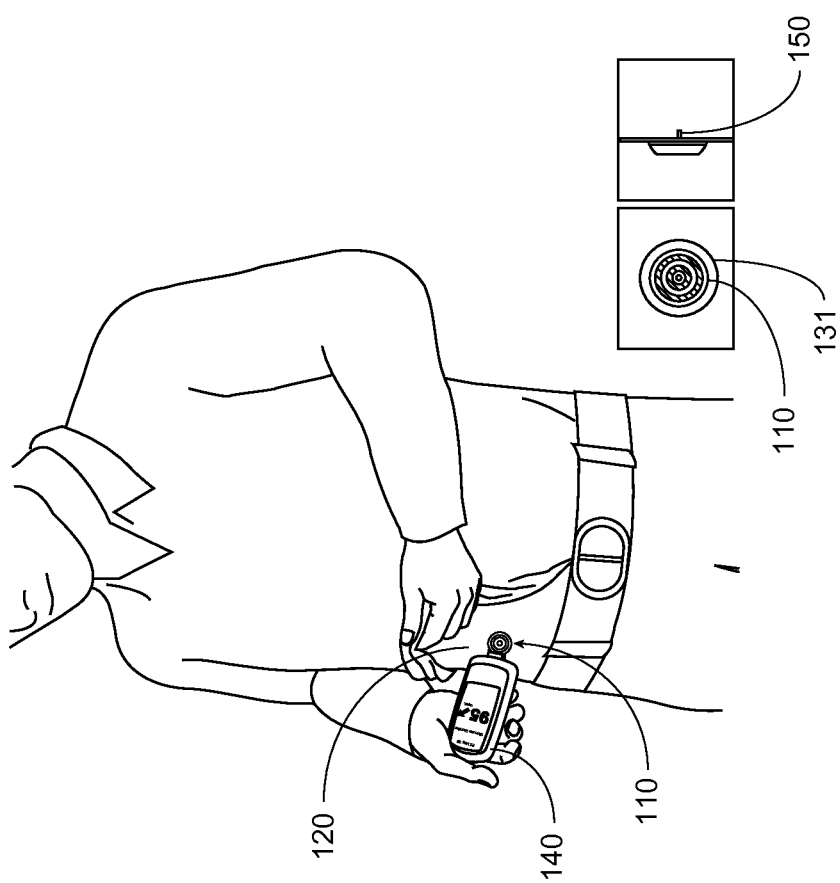
FIG. 1 illustrates an overall system of the analyte monitoring system, according to certain embodiments.

FIG. 1 illustrates an overall system of the analyte monitoring system including real time data acquisition related to embodiments of the present disclosure. Referring to FIG. 1, analyte monitoring system 100 is shown and comprises on-body housing 110 that is positioned or adhered to the skin surface 120 of the user or the patient using, for example, an adhesive 131 to retain the position of the on-body housing 110 on the skin surface during the monitoring time period such as, for example, about 10 days or more. Referring to FIG. 1, as shown, when the user or the patient wishes to determine the analyte concentration, the reader (e.g., blood glucose meter) 140 is positioned such that it contacts or touches the on-body housing 110 as shown. In certain embodiments, the physical contact or touching of the on-body housing 110 with the reader 140 transfers one or more signals from the electronics contained within the on-body housing 110 to the reader 140 via electrical communication. The transferred or provided signals may include signals corresponding to the real time analyte concentration level such as, for example, real time glucose level information, monitored analyte concentration trend information such as, for example but not limited to, the previous three hours, the rate of change of the analyte concentration determined based at least in part of the monitored analyte concentration trend information, or one or more combinations thereof.

Referring again to FIG. 1, it can be seen from the middle insert figure that an in-vivo analyte sensor 150 may be transcutaneously positioned such that a portion of the analyte sensor is positioned and retained under the skin layer during the monitoring time period of approximately, for example, but not limited to ten days, and further, that the in-vivo analyte sensor 150 is coupled to the on-body housing 110 such that the electrodes (working and counter electrodes, for example) of the in-vivo analyte sensor 150 are electrically coupled to one or more electrical components in the on-body housing 110 and configured to process and store, among others, the signals from the in-vivo analyte sensor 150. Furthermore, by way of nonlimiting comparison, as discussed above, embodiments including self-powered analyte sensor which in some embodiments does not need an external power supply and the touch based analyte data acquisition/communication with obviates the need for a wireless data communication component, permits the sizing of the on-body housing 110 to be approximately the size of a dime. After the monitoring time period, the in-vivo analyte sensor 150 and/or on-body housing 110 may be removed, disposed, and replaced.

FIG. 2 illustrates an exploded perspective view of the components of another exemplary analyte monitoring system, in accordance with certain embodiments of the present disclosure. Referring to FIG. 2, as shown, embodiments include a reader 240 that is provided with probes 211a, 211b, 211c configured to make electrical contact with the respective one of the concentric electrical contacts 220 on the on-body housing 210 connected to an in-vivo analyte sensor 250. As can be seen, embodiments include the probes 211a, 211b, 211c at a predetermined position on the housing of the reader 240, and at a position relative to each other such that when the reader 240 is positioned in contact with the on-body housing 210, each of the probes 211a, 211b, 211c of the reader 240 makes physical contact with the respective one of the concentric electrical contacts 220 on the on-body housing 210.

The in-vivo analyte sensor 250 extends from the on-body housing 210 to transcutaneously position electrodes (e.g., working and counter electrodes) on the in-vivo analyte sensor 250 under the skin layer of a user. The electrodes of the in-vivo analyte sensor 250 are electrically coupled to one or more electrical components or sensor electronics in the on-body housing 210. Such electronics are configured to process and store the signals from the in-vivo analyte sensor 250. After the monitoring time period, the in-vivo analyte sensor 250 and/or on-body housing 210 may be removed, disposed, and replaced.

Referring to FIG. 2, while embodiments include concentric electrical contacts configuration on the on-body housing 210, in accordance with the embodiments of the present disclosure, the electrical contacts may include other shapes and sizes such as spaced apart probes, contact pads, oval shaped contacts, and any other suitable configuration to easily establish the electrical contact with the respective of the probes 211a, 211b, 211c on the in-vivo 240 when the in-vivo 240 is brought into contact with the on-body housing 210.

Figure 3:
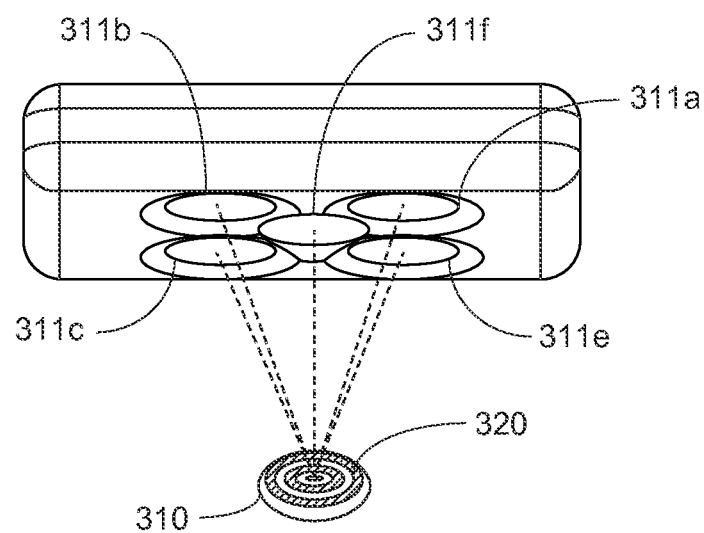
FIG. 3 illustrates a perspective view of electrical contacts of an on body housing that are coupleable to corresponding contacts on an analyte reader, according to certain embodiments.

FIG. 3 illustrates a perspective view of on-body housing electrical contacts coupleable to the electrode contacts on the reader, in accordance with some embodiments of the present disclosure. Referring to FIG. 3, the reader includes a plurality of mating or contact sites 311a, 311b, 311c, 311d, 311e, where each of the plurality of contact sites 311a, 311b, 311c, 311d, 311e include probes to establish electrical contact with the corresponding one of the concentric electrical contacts 320 on the on-body housing 310. That is, in certain embodiments, to facilitate alignment of the probes of the receiver unit or the blood glucose meter to the concentric electrical contacts 320 of the on-body housing 310, the receiver unit or the blood glucose meter may be provided with multiple contact sites 311a, 311b, 311c, 311d, 311e such that any one of the five contact sites 311a, 311b, 311c, 311d, 311e shown in FIG. 3 may transfer the signals generated from the in-vivo analyte sensor to the reader.

In certain instances, the plurality of contact sites 311a, 311b, 311c, 311d, 311e may be provided on an outer housing surface of the reader, where each of the plurality of contact sites 311a, 311b, 311c, 311d, 311e are beveled or include a groove so as to facilitate the mating with the respective concentric electrical contacts on the on-body housing. In some instances, geometries and/or configurations of the mating sites on the reader or the on-body housing may facilitate and/or aid the physical connection between the two components during analyte sensor data acquisition to determine real time analyte concentration level and/or trend information. For example, each contact site 311a, 311b, 311c, 311d, 311e of the reader may include a rail or protrusion that aligns with a corresponding respective groove on the on-body housing 310 to guide, aid, and/or facilitate the alignment or proper positioning of the contact probes on the reader to the respective concentric electrical contacts on the on-body housing 310. Such a groove on the on body housing 310 in certain embodiments may minimize interference and/or discomfort while wearing the on-body housing on the skin surface during the monitoring time period of for example, about ten days.

Figure 4:
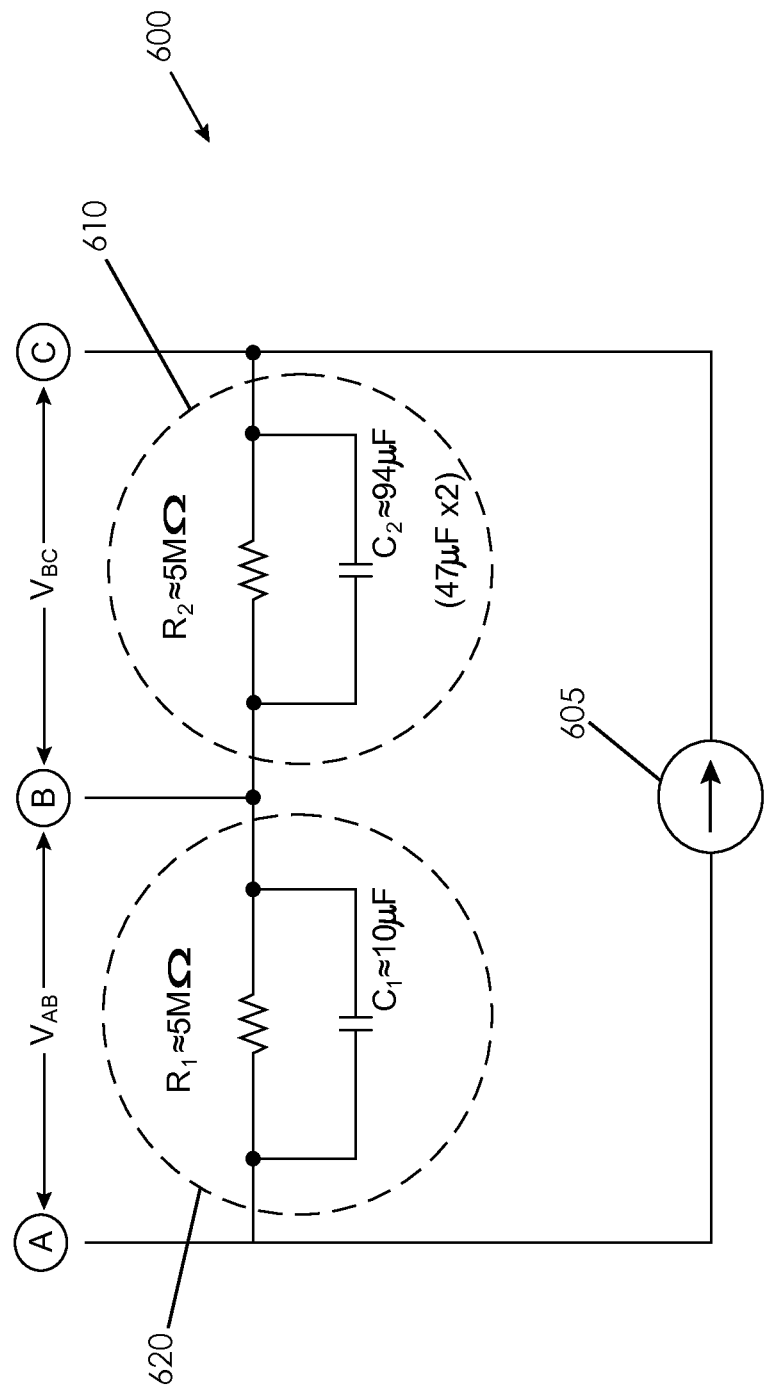
FIG. 4 illustrates a circuit diagram of a self-powered on-body unit, according to certain embodiments.

FIG. 4 illustrates a circuit diagram of a self-powered OBU, according to certain embodiments. As shown, the electronics within the OBU includes two resistor-capacitor (RC) pairs 610 and 620 that are provided in series. RC pair 620 is shown comprising R1 in parallel with C1. RC pair 610 is shown comprising R2 in parallel with C1. In the example shown, resistor R1 is approximately 5 MΩ and capacitor C1 is approximately 10 µF; and resistor R2 is approximately 5 MΩ and capacitor C2 is approximately 94 µF. The embodiment shown includes approximate resistance values of resistors R1 and R2 at room temperature (approximately 25° C.). Some embodiments include such relatively high resistance values to increase the voltage signal across the working and counter electrodes of the in-vivo analyte sensor. It should be appreciated that the values shown are exemplary and that other values may be implemented in other embodiments. For example, C2 may be provided by one or more capacitors, and R1,R2 may be implemented as resistors or thermistors.

Node A is shown at one end of the first RC pair; node B between the two RC pairs; and node C at the other end of the second RC pair. Current source 605 is shown across nodes A and C and represents the current flow provided to circuit 600 by the in-vivo analyte sensor when contacting interstitial fluid under a skin layer.

The working electrode of the in-vivo analyte sensor is electrically connected to node A, and the counter electrode of the in-vivo analyte sensor is electrically connected to node C. When the in-vivo sensor contacts interstitial fluid, for example, current flow is generated from the resulting chemical reaction that takes place. For example, current within the nanoamp (nA) range may be generated and provided to the RC pairs of the electronic circuit.

Figure 5A:
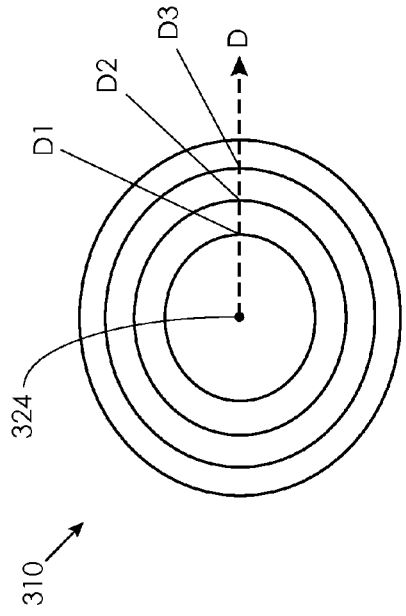
FIGS. 5A and 5B illustrate a perspective view and top view, respectively, of an on-body housing, according to certain embodiments.
Figure 5B:
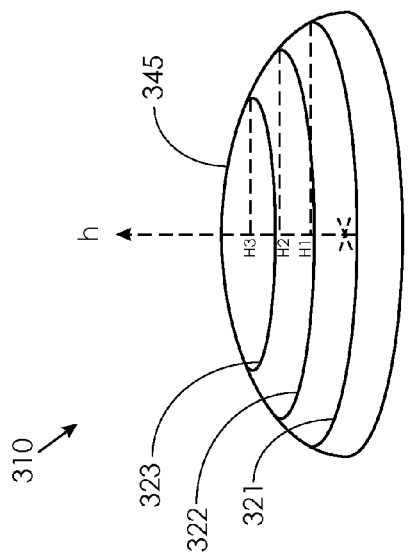

Concentric electrical contacts (not shown) are disposed externally on the housing of the OBU (e.g., as shown in FIGS. 5A and 5B) and are each coupled to a respective node A, B, and C in the electronic circuit shown in FIG. 4. In this way, one concentric electrical contact is provided at the working electrode (node A), another concentric electrical contact at the counter electrode (node C), and yet another concentric electrical contact between the two RC pairs (node B).

The circuit shown enables measurements to be taken that are indicative of analyte concentrations detected by the in-vivo analyte sensor. Vab is the voltage across the first RC pair (e.g., across nodes A and B) and reflects the current glucose measurement, as filtered based on the R1*C1 time constant. Vbc is the voltage across the second RC pair (e.g., across nodes B and C) and reflects the average glucose value over a longer period of time, as determined by the R2*C2 time constant. Furthermore, the difference between the two voltage readings Vab and Vbc represents trend information for the detected analyte concentrations.

OBUs and On-Body Housings

In some aspects of the present disclosure, voltage measurements from the OBU may be acquired by an analyte reader (e.g., a blood glucose meter) that is brought into physical contact with the OBU. Electrical contacts on the reader contact the concentric electrical contacts on the OBU and enable the appropriate measurements to be communicated to the reader. Having good electrical contact between the reader and the OBU is important in ensuring accurate readings are obtained. For example, accumulation of water or liquids on the housing of the OBU can lead to faulty readings by providing a conductive parallel path to R1 and/or R2 which alters the corresponding voltage measurement.

The on-body housing includes a substantially flat surface and a curved and convex surface that is opposite of the substantially flat surface. The substantially flat surface may include adhesive, for example, that is used to apply the OBU to the surface of a body part. The substantially flat surface contacts and sticks to the skin surface, while the curved and convex surface extends outward away from the substantially flat surface and skin surface. The substantially flat surface is thus sometimes referred to herein as the "bottom surface" and the curved and convex surface sometimes referred to herein as the "top surface".

The top surface of the on-body housing includes the concentric electrical contacts that contact the reader when the reader is brought into contact with the top surface of the housing. The term "top surface" is used herein to refer generally to the surface of the housing that is opposite the substantially flat surface and skin surface (when the OBU is attached to the skin).

The surface contour of the top surface of the on-body housing can affect the amount of accumulation of water or other fluids on the housing, and thus affect the adequacy of the electrical contact between the OBU and the reader. For instance, an on-body housing with a flat or level top surface enables water or other liquids to accumulate on the top surface of the housing, increasing the likelihood of a false reading. Furthermore, liquids may accumulate in OBU housings having top surface contours that include recessed, depressed, or concave top surface contours. Furthermore, a top surface that is generally concave would extend generally inward towards the substantially flat surface of the on-body housing (or towards the body part when the OBU is attached to a body part). The concave contour would form depositories on the top surface for liquid to collect and create conductive parallel paths which would corrupt readings.

In certain aspects of the present disclosure, the OBU includes an on-body housing that has a substantially flat surface and a curved and convex surface that is opposite of the substantially flat surface. The "convex" surface extends generally outward away from the substantially flat surface and skin surface (when the OBU is attached to the body part). In this way, the OBU is adapted to have a surface contour that is conducive to avoiding accumulation of water or other liquids that could interfere with the measurements. The surface contour of the housing is such that the water or other liquids tend not to pool or otherwise collect on the top surface of the housing.

In certain embodiments, the OBU includes a housing that is dome-shaped. The dome-shaped housing includes a top surface that is curved and convex. It should be appreciated that the dome-shaped housing may comprise a top surface having a variety of shapes—e.g., spherical, ellipsoidal, or any other curved and convex surface contour. It should also be appreciated that a curved surface contour that is referred to as spherical and/or ellipsoidal does not necessarily require that the contour be a complete sphere or ellipsoid, but rather may be part of a sphere or ellipsoid. For example, the contour may be a semi-spherical, quarter-spherical, or other fractional piece of a sphere. The same applies to other surface contours such as ellipsoids.

It should also be appreciated that the shapes of the surface contours described above are not required to be exact, but rather may be substantially or approximately the shape that is described. For example, a surface that is referred to as spherical shaped also includes surfaces that are substantially spherical or approximately spherical.

It should also be appreciated that the curved and convex surface includes contours in two dimensions that may each be independently circular, elliptical, oval, or otherwise curved and convex. For example, an ellipsoidal surface contour may include a circular contour viewed from one direction and an elliptical contour viewed from another direction.

The substantially flat base of the on-body housing may also vary in shape. In some embodiments, the substantially flat base is circular. In other embodiments, the substantial flat base is elliptically shaped. In yet other embodiments, the substantially flat base is another regular or irregular shape.

FIGS. 5A and 5B illustrate a perspective view and top view, respectively, of an on-body housing of an OBU, according to some embodiments. In the embodiment shown, the on-body housing 310 is dome-shaped. The top surface 345 of the housing 310 is curved and convex. It should be appreciated that the curvature may vary in different embodiments. For example, the surface contour of the top surface 345 of the housing 310 may have circular, elliptical, parabolic, or other curved contours that do not provide a flat or concave top surface that may accumulate water or other liquid on the top surface of the OBU.

On-body housing includes electrical contacts 321, 322, and 323 disposed on the top surface of the housing. In the embodiment shown, the electrical contacts are concentric electrical contacts that are disposed externally at different heights (H) on the top surface of the on-body housing. Concentric electrical contacts 321, 322, and 323 are disposed on the external side of the on-body housing 310 that contacts the reader (not shown). Concentric electrical contact 322 is disposed on the on-body housing 310 concentrically around concentric electrical contact 323. Concentric electrical contact 321 is disposed on the on-body housing concentrically around concentric electrical contact 322. In the embodiment shown, the concentric electrical contacts 321, 322, and 323 are each ring-shaped and disposed on a dome-shaped on-body housing 310 with the center of the rings aligned with a center 324 of the on-body housing 310. It should be appreciated that the concentric electrical contacts 321, 322, and 323 may be approximately centered with respect to the center of the housing.

A height axis H is shown in FIG. 5A for reference purposes. Concentric electrical contact 321 is shown at a height H1; concentric electrical contact 322 is shown at a height H2; concentric electrical contact 323 is shown at a height H3; and the center 324 of the on-body housing 310 is shown at a height H4. It should be appreciated that the height of each concentric electrical contact 321, 322, and 323 on the on-body housing 310 may vary. In some embodiments, the concentric electrical contacts are equidistantly spaced in height—e.g., the distance between H1 and H2 is equal to the distance between H2 and H3. In some embodiments, the concentric electrical contacts 321, 322, and 323 are not equidistantly spaced in height.

As shown in FIG. 5B, concentric electrical contact 323 is shown a distance D3 from center 324; concentric electrical contact 322 is shown a distance D2 from concentric electrical contact 323; and concentric electrical contact 321 is shown a distance D1 from concentric electrical contact 322. In some embodiments, these distances of the concentric electrical contacts are equidistantly spaced—e.g., the distance between D1 and D2 is equal to the distance between D2 and D3. In other embodiments, these distances of the concentric electrical contacts are not equidistantly spaced.

As shown in FIGS. 5A and 5B, the top surface 345 of the housing is curved and convex such that any water or liquid on the housing will not accumulate on the top surface and create conductive parallel paths which alter readings. As concentric electrical contacts 321, 322, and 323 are disposed on the curved and convex top surface, water or other fluid accumulation is minimized or avoided between the electrical contacts 321, 322, and 323.

It should be appreciated that in some alternative embodiments, concentric electrical contact 323 may be a solid circular shape instead of ring-shaped. For example, concentric electrical contacts 322 and 321 may be concentrically disposed around concentric electrical contact 323.

Figure 6A:
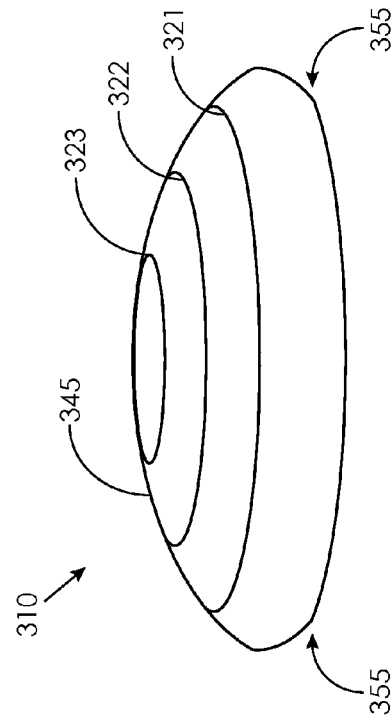
FIG. 6A illustrates a perspective view of a dome-shaped on-body housing with a base perimeter that is flat, according to certain embodiments.

In certain embodiments, the base perimeter of the housing comprises a flat edge. For example, FIG. 6A illustrates a perspective view of a dome-shaped on-body housing with a base perimeter that has flat edge, according to certain embodiments. As shown, housing 310 includes curved and convex surface 345 and concentric electrical contacts 321, 322, and 323 disposed thereon. As shown, the base perimeter of the housing 310 includes a flat edge 350.

Figure 6B:
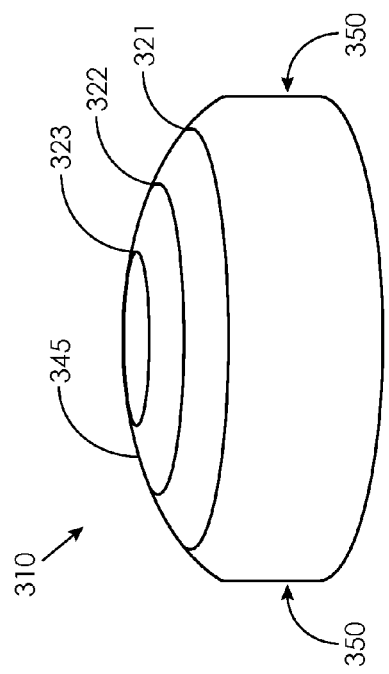
FIG. 6B illustrates a perspective view of a dome-shaped on-body housing with a base perimeter that is recessed, according to certain embodiments.

In other embodiments, the base perimeter of the housing is recessed inward—e.g., decreases in width (e.g., decreasing in cross-sectional diameter when viewed from the top). For example, FIG. 6B illustrates a perspective view of a dome-shaped on-body housing with a recessed base perimeter, according to certain embodiments. As shown, housing 310 includes curved and convex surface 345 and concentric electrical contacts 321, 322, and 323 disposed thereon. As shown, the housing 310 includes a recessed base perimeter 355.

Figure 7:
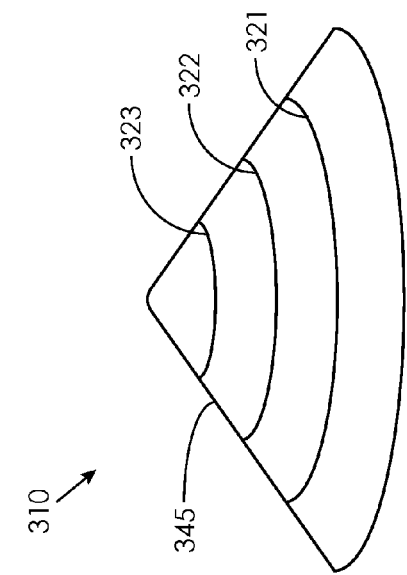
FIG. 7 illustrates a perspective view of an on-body housing that is cone-shaped, according to certain embodiments.

In certain embodiments, the housing is cone-shaped. The cone-shaped housing may include any variety of cone shapes—e.g., standard conical, bi-conical, power series (also known as parabolic), etc. For example, FIG. 7 illustrates a perspective view of an on-body housing that is cone-shaped, according to certain embodiments. In the embodiment shown, concentric electrical contacts 321, 322, and 323 are disposed externally on the top surface 345 of the on-body housing 310 that contacts the reader (not shown). Concentric electrical contact 322 is disposed on the on-body housing 310 concentrically around concentric electrical contact 323. Concentric electrical contact 321 is disposed on the on-body housing concentrically around concentric electrical contact 322. In the embodiment shown, the concentric electrical contacts 321, 322, and 323 are each ring-shaped and disposed on the top surface 345 of the housing with the center of the rings aligned with a center 324 of the on-body housing 310. In some alternative embodiments, the housing 310 may include a base perimeter with a flat edge or recessed base perimeter, as described above.

It should be appreciated that the above described embodiments are exemplary and that other shape of the housing may be implemented in alternative embodiments. The shape of the top surface of the housing should prevent water or other liquids from pooling or otherwise collecting on the exterior of the housing—e.g., within recesses or containers formed by the contour of housing.

Figure 8:
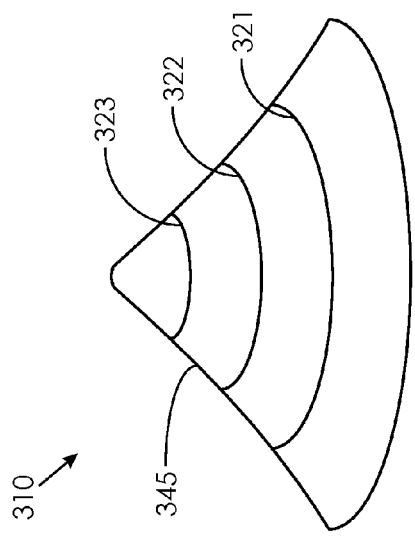
FIG. 8 illustrates a perspective view of an on-body housing, according to certain embodiments.

For example, FIG. 8 illustrates a perspective view of an on-body housing, according to certain embodiments. In the embodiment shown, housing 310 includes a top surface 345 that is curved and convex. While top surface 345 includes portions of the contour that are curving upwards, the surface 345 as a whole is convex and extends generally outward from the substantially flat base without any recesses, depressions, or concave portions that form depositories in which fluid may accumulate on the top surface of the housing.

Concentric electrical contacts 321, 322, and 323 are disposed externally on the top surface of the on-body housing 310 that contacts the reader (not shown). Concentric electrical contact 322 is disposed on the on-body housing 310 concentrically around concentric electrical contact 323. Concentric electrical contact 321 is disposed on the on-body housing concentrically around concentric electrical contact 322. In the embodiment shown, the concentric electrical contacts 321, 322, and 323 are each ring-shaped and disposed on a dome-shaped on-body housing with the center of the rings aligned with a center 324 of the on-body housing 310. As the concentric electrical contacts 321, 322, and 323 are disposed on a curved and convex surface of the housing 310, water or other fluids are prevented from accumulating such that a parallel conductive path would form. In some alternative embodiments, the housing 310 may include a base perimeter with a flat edge or recessed, as described above.

It should be appreciated that in some alternative embodiments, concentric electrical contact 323 may be a solid circular shape instead of ring-shaped. For example, concentric electrical contacts 322 and 321 may be concentrically disposed around concentric electrical contact 323.

Testing for Sufficient Contact with an OBU

In some aspects of the present disclosure, methods and techniques for verifying adequate electrical contact with an OBU, such as ones described herein, are provided. Achieving good electrical contact between the on-body housing and the reader (e.g., glucose meter or other analyte meter) enables successful measurement readings to be obtained. As previously stated, the mechanical design of the OBU and the reader may increase the robustness of the electrical contacts. In some instances, electrical continuity tests may be performed to ensure that the reader is making good electrical contact with the OBU. While continuity tests may be made using the concentric electrical contacts 321, 322, and 323, the continuity measurement may potentially corrupt the voltage across one or both RC pairs 610,620. This can occur because continuity measurements may involve injecting a current across one or both of the resistors, thereby changing the voltage across one or both RC pairs 610,620.

In some aspects of the present disclosure, one or more isolated contacts may be disposed externally on the on-body housing and used to perform continuity measurements. The isolated contacts are different from the concentric electrical contacts 321, 322, and 323 and are isolated from both of the RC pairs. The quantity, shape, and location of the isolated contacts on the top surface of the on-body housing may vary—e.g., as demonstrated in FIGS. 9 and 10.

Figure 9B:
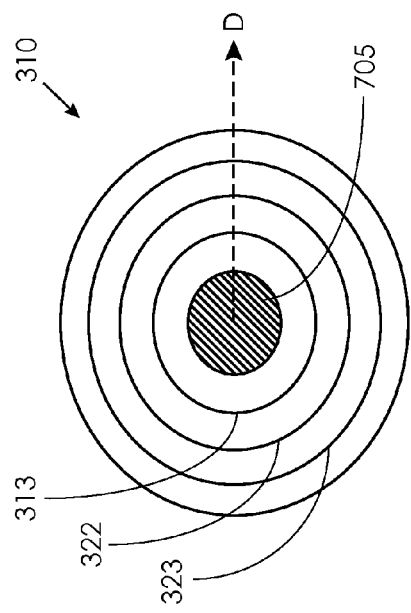
FIGS. 9A and 9B illustrate a perspective view and top view, respectively, of an on-body housing having isolated electrical contacts, according to certain embodiments.
Figure 9A:
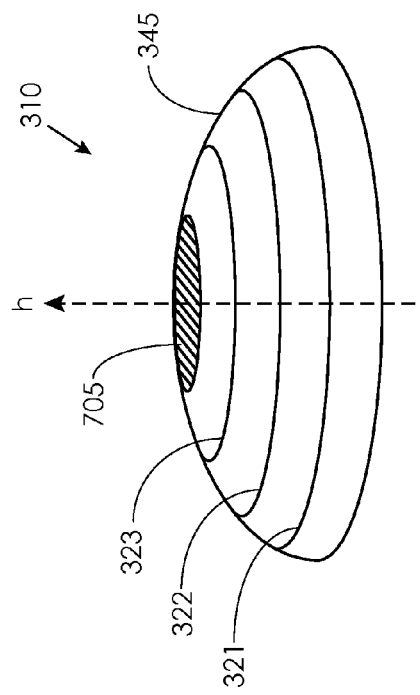

FIGS. 9A and 9B illustrate a perspective view and top view of an on-body housing of an OBU, according to some embodiments. In the embodiment shown, the concentric electrical contacts 321, 322, and 323 are disposed externally on on-body housing 310. Concentric electrical contacts 321, 322, and 323 are disposed on the top surface of the on-body housing 310 with concentric electrical contact 321 disposed around concentric electrical contact 322, which is disposed around concentric electrical contact 323. Again, concentric electrical contacts 321, 322, and 323 are ring-shaped and disposed on a dome-shaped on-body housing with the center of the rings aligned with a center 324 of the on-body housing 310.

The embodiment shown in FIGS. 9A and 9B differ from the embodiment shown in FIGS. 5A and 5B by having a set of isolated contacts 705 disposed externally on the on-body housing 310. The set of isolated contacts 705 is separate from the concentric electrical contacts 321, 322, and 323 and isolated from both RC pairs 610, 620 (shown in FIG. 4). The set of isolated contacts 705 contact the corresponding contact elements disposed on the reader and enable a continuity test to be performed via the isolated contacts 705. As the isolated contacts 705 are isolated from the concentric electrical contacts 321, 322, and 323 and isolated from both RC pairs 610, 620, any current provided by the continuity test does not disturb or corrupt the voltage signals across the concentric electrical contacts 321, 322, and 323, and thus does not alter the voltages across one or both RC pairs 610, 620.

In the embodiment shown, the set of isolated contacts 705 are disposed on the on-body housing 310 with the concentric electrical contacts 323. It should be appreciated that the set of isolated contacts 705 may comprise a plurality of contacts positioned in any variety of arrangements. FIGS. 10A-10D illustrate top views of an OBU with a set of isolated contacts, according to certain embodiments. As shown, OBU comprises an on-body housing 310; concentric electrical contacts 321, 322, and 323; and a set of isolated contacts 705. The set of isolated contacts 705 are shown comprising isolated contacts 705A and 705B. It should be appreciated that a different number of isolated contacts other than two may be implemented in other embodiments.

Figure 10A:
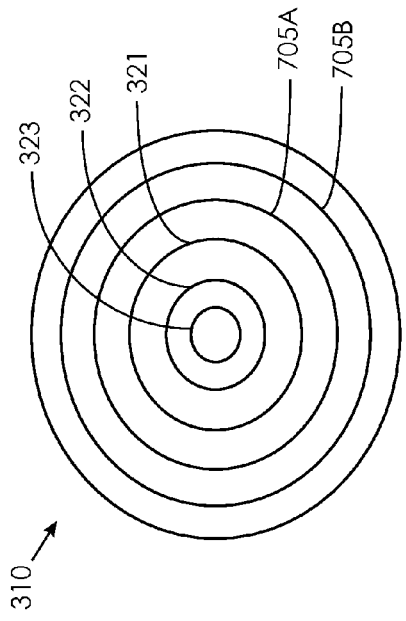
FIG. 10A illustrates an on-body housing having two isolated contacts, according to certain embodiments.

In FIG. 10A, both isolated contacts 705A and 705B are concentric electrical contacts that are disposed externally on the top surface 345 of the on-body housing 310 within concentric electrical contact 323. Put another way, isolated contacts 705A and 705B are disposed within all three concentric electrical contacts 321, 322, and 323. Both isolated contacts 705A and 705B are ring-shaped and centered with respect to the center of the on-body housing 310.

Figure 10B:
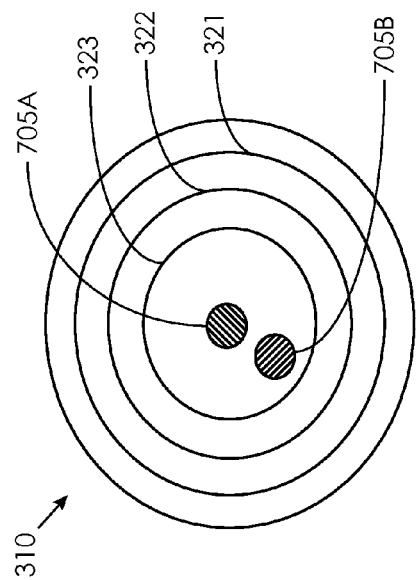
FIG. 10B illustrates an on-body housing having two isolated contacts, according to certain embodiments.

In FIG. 10B, both isolated contacts 705A and 705B are concentric electrical contacts that are disposed externally on the top surface 345 of the on-body housing 310. Isolated contact 705A is a solid circular electrical contact disposed within the innermost concentric electrical contact 323, and isolated contact 705B is a ring-shaped electrical contact that is concentrically disposed around the three concentric electrical contacts 321, 322, and 323. Thus, the three real signals on the three concentric electrical contacts 321, 322, and 323 are disposed between the pair of isolated contacts 705A and 705B. In this way, if there is continuity between the isolated contacts 705A and 705B, then the reader is correctly positioned on the OBU and the reader connection is in correct alignment for proper contact with the three concentric electrical contacts 321, 322, and 323 disposed between the pair of isolated contacts 705A and 705B. It should be appreciated that the configuration of having the concentric electrical contacts 321, 322, and 323 disposed between the pair of isolated contacts 705A and 705B may also apply to the other embodiments (e.g., the embodiments shown FIGS. 10A, 10C, and 10D, and variations thereof).

Figure 10C:
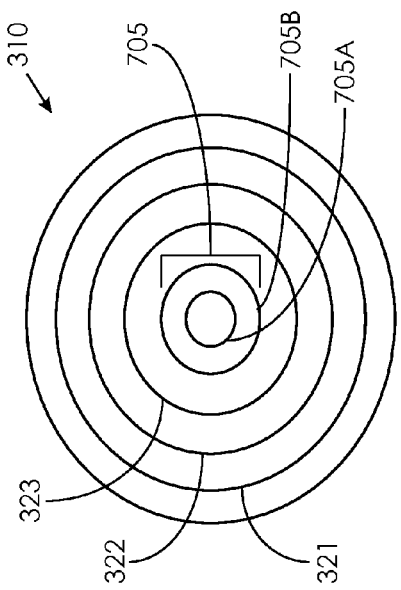
FIG. 10C illustrates an on-body housing having two isolated contacts, according to certain embodiments.

In FIG. 10C, both isolated contacts 705A and 705B are concentric electrical contacts that are disposed externally on the top surface 345 of the on-body housing 310 outside concentric electrical contact 323. Both isolated contacts 705A and 705B are ring-shaped and centered with respect to the center of the on-body housing 310. In the embodiment shown, both isolated contacts 705A and 705B are disposed outside concentric electrical contact 321.

Figure 10D:
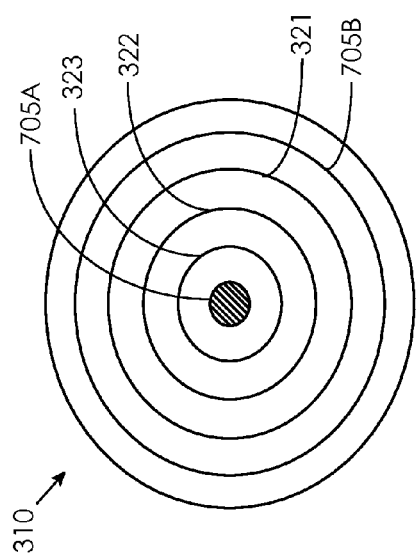
FIG. 10D illustrates an on-body housing having two isolated contacts, according to certain embodiments.

In FIG. 10D, both isolated contacts 705A and 705B are solid circular electrical contacts that are disposed externally on the top surface 345 of the on-body housing 310 within concentric electrical contact 323. Isolated contact 705A is centered with respect to the center of the on-body housing, and isolated contact 705B is not.

It should be appreciated that the shape and position of the corresponding contacts on the reader may vary but should enable appropriate contact with the arrangement of isolated contacts 705 when the reader is brought in contact with the OBU. For example, in some embodiments, the reader includes concentric electrical contacts that line up with the electrical contacts on the OBU. It should be appreciated that the embodiments shown enable the reader to be placed on the OBU irrespective of orientation and still permit contact with the electrical contacts on the OBU. For example, the reader may include ring-shaped concentric electrical contacts with the same diameter as the corresponding electrical contacts on the OBU. Or as another example, the reader may include electrical contacts that are not ring shaped but disposed at the appropriate distance from center to come in contact with the corresponding concentric electrical contacts on the OBU. It is noted that in FIG. 10D, the OBU and reader may still be brought in contact irrespective of orientations—e.g., if the reader includes a concentric electrical contact that has a diameter that aligns with isolated contact 705B. it should also be appreciated that the reader may include an interface that is designed to physically mate with or "fit" with the OBU to further promote a good electrical connection.

Figure 11:
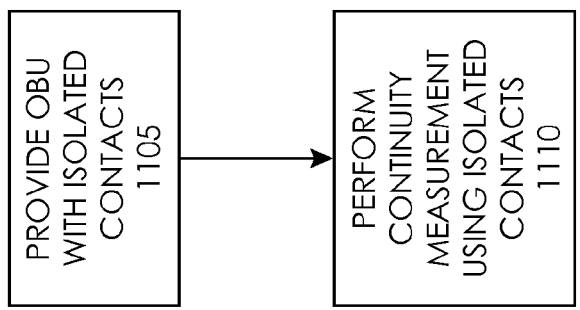
FIG. 11 illustrates a flowchart for a method for performing a continuity measurement on an on-body unit, according to certain embodiments.

FIG. 11 illustrates flowchart for performing a continuity measurement on an OBU, according to certain embodiments. In block 1105, an OBU having isolated contacts is provided. For example, the on-body housings 310 described in FIGS. 9A-9B and FIGS. 10A-10D may be provided for performing a continuity measurement. The OBU may, in some instances, already be attached to a body part. In other instances, the OBU may be unattached to a body part during continuity testing. In block 1110, a continuity measurement is performed using the isolated contacts. As stated above, the set of isolated contacts contact the corresponding contact elements disposed on the reader and enable a continuity test to be performed via the isolated contacts 705. As the isolated contacts 705 are isolated from the concentric electrical contacts 321, 322, and 323 (or other type of electrical contacts coupled to nodes A, B, and C in FIG. 4), any current provided by the continuity test does not disturb or corrupt the voltage signals across the RC pairs 610 and 620.

In certain aspects of the present disclosure, a continuity test is performed across only one of concentric electrical contacts 321, 322, or 323. In this way, test current is not injected across one or both capacitors, resulting in altered voltages across the capacitors and thus in accurate readings. For example, the reader may be adapted to include test contacts that contact one of the concentric electrical contacts 321, 322, and 323 when the reader and OBU are brought together for a test. If, for instance, a complete circuit is established by the concentric electrical contact, then sufficient contact is achieved and indicated to the user. If, however, a completed circuit is not established, then the insufficient contact is indicated to the user. As the single concentric electrical contact provides a short circuit to complete the circuit.

Figure 12:
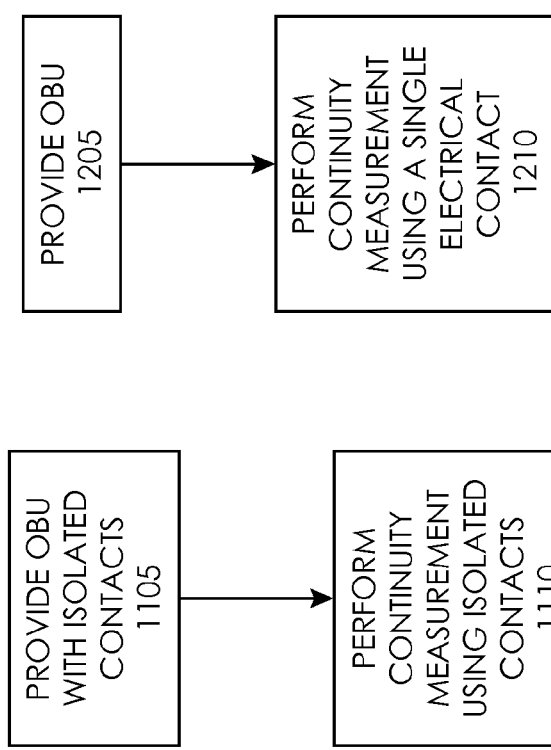
FIG. 12 illustrates a flowchart for a method for performing a continuity measurement on an on-body unit, according to certain embodiments.

FIG. 12 illustrates a flowchart for performing a continuity measurement on a single electrical contact on the OBU, according to certain embodiments. In block 1105, an OBU is provided. For example, the OBU may include concentric electrical contacts disposed on an on-body housing such as shown in FIGS. 5-8. In block 1110 a continuity measurement is performed on one of the concentric electrical contacts 321, 322, and 323 electrically connected to nodes A, B, and C in FIG. 4. The continuity measurement is performed on the single electrical contact and does not disturb or corrupt the voltage signals across either of the RC pairs 610 and 620.

It should be appreciated that, in some instances, the continuity measurement as described in FIG. 12 may be performed on an OBU having isolated contacts 705. Such continuity measurement may be performed on either the isolated contacts and/or the concentric electrical contacts 321, 322, and 323 (electrically coupled to nodes A, B, and C in FIG. 4).

As stated earlier, continuity measurements can corrupt the voltage signals Vab and Vbc, as represented in FIG. 4. Continuity measurements involve injecting current (I) into the path under test for a period of time (T), and the capacitors C1 and C2 in the circuit will accumulate charge (Q) based on the equation: Q=IT. Thus, the voltages across the capacitors C1 and C2 are altered by the injected current. Furthermore, the injected current that tests for continuity may be on the order of microamps as compared to nanoamps generated by the self powered OBU, thus significantly affecting the voltage signals Vab and Vbc.

Figure 13:
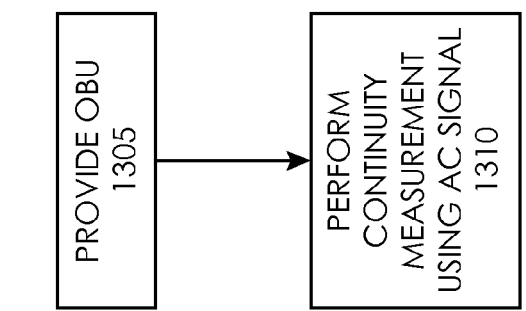
FIG. 13 illustrates a flowchart for a method for performing a continuity measurement on an on-body unit, according to certain embodiments.

In certain aspects of the present disclosure, an alternating current (AC) signal is provided to perform the continuity measurement using electrical contacts electrically connected to nodes A, B, and C in FIG. 4 (e.g., concentric electrical contacts 321, 322, and 323). FIG. 13 illustrates a flowchart for performing a continuity measurement on an OBU with an AC signal, according to certain embodiments. As shown by block 1305 an OBU, such as one described herein, is provided. The OBU may be coupled to a body part in some instances, or not coupled to a body part in other instances. As shown in block 1310, a continuity measurement is then performed on the OBU using an AC signal. For example, an analyte meter may be configured to couple to the OBU and perform the continuity measurement automatically or as initiated by the user.

In certain embodiments, the AC signal is a sine wave current that is applied for one or more full cycles. Any current flowing in one direction is offset by the equal amount of current flowing in the opposite direction, thus resulting in no net energy residing in the OBU (e.g., no net charge accumulation in the capacitors C1 or C2). The continuity measurement thus does not affect the voltage signals Vab and Vbc. It should be appreciated that in other embodiments, the AC signal may be implemented as another waveform than a sine wave—e.g., square wave, triangle wave, etc.

In certain aspects of the present disclosure, a DC current pulse is used to perform the continuity measurement using electrical contacts electrically connected to nodes A, B, and C in FIG. 4 (e.g., concentric electrical contacts 321, 322, and 323). The DC current pulse is applied across two of the electrical contacts in one direction for a period of time (t). A DC current pulse of the same value as the first is then applied across the same two electrical contacts in the opposite direction for the same period of time (t). In this way, no net energy resides in the OBU (e.g., no net charge accumulation in C1 or C2), and the signal of interest (e.g., glucose signal) is not altered or perturbed. Moreover, using a small pulse decreases any negative influence by the continuity measurement. For example, because charge is equal to the product of current and time, the smaller the duration of the current (e.g., a small pulse), the smaller the charge accumulated.

Figure 14:
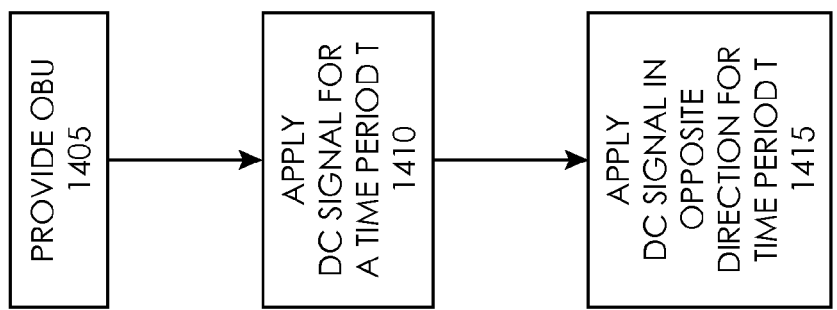
FIG. 14 illustrates a flowchart for a method for performing a continuity measurement on an on-body unit, according to certain embodiments.

FIG. 14 illustrates a flowchart for performing a continuity measurement on an OBU, according to certain embodiments. As shown by block 1405 an OBU, such as one described herein, is provided. The OBU may be coupled to a body part in some instances, or not coupled to a body part in other instances. As shown in block 1310, a continuity measurement is then performed on the OBU using the DC pulse signals described above. For example, the reader may be configured to couple to the OBU and perform the continuity measurement automatically or as initiated by the user. For instance, the DC current pulse may be provided in one direction across two of the concentric electrical contacts 321, 322, and 323 for a predetermined amount of time Immediately thereafter, and without requiring the reader to be moved, another DC current pulse of the same value and duration is provided in the opposite direction across the same two concentric electrical contacts. In this way, no net energy resides in the OBU (e.g., no net charge accumulation in C1 or C2), and the signal of interest (e.g., glucose signal) is not altered or perturbed.

In some instances, the measurement accuracy of analyte sensors is dependent upon temperature. As such, in some embodiments, a temperature sensor is provided with the OBU to measure body temperature at or near the analyte sensor. The temperature reading can then be used to calibrate the measurement readings accordingly. The temperature sensor may be internal or external to the on-body housing. The temperature sensor may also sit above the skin, or be provided as an electrode running along the analyte sensor to be transcutaneously implanted below the skin. The temperature sensor electrode would then be electrically coupled to a temperature measurement circuit within the on-body housing. The temperature measurements may be transmitted to the blood glucose meter upon request. For manufacturability and cost-effectiveness, particularly when the on-body housing is intended to be disposable, it may be desirable to avoid the inclusion of a temperature sensor and/or control circuitry in the on-body housing. As such, in one embodiment, there is provided reader (e.g., a blood glucose meter, or other hand-held measurement or analysis instrument) with a temperature measurement sensor and control system. The temperature measurement sensor may be provided on the permanent hand-held instrument to avoid disposing of the temperature measurement components when the on-body housing is disposed. In some embodiments, a metal bridge may be disposed on the OBU to test for continuity and to measure temperature. Additional details regarding metal bridges that may be implemented on the OBU may be found in U.S. Pat. No. 5,711,607, issued Jan. 27, 1998, the entirety of which is incorporated herein by reference.

Analytes that may be monitored include, but are not limited to, acetyl choline, amylase, bilirubin, cholesterol, chorionic gonadotropin, creatine kinase (e.g., CK-MB), creatine, creatinine, DNA, fructosamine, glucose, glutamine, growth hormones, hormones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times. In one embodiment, the analyte sensor is a glucose sensor. In another embodiment, the analyte sensor is a ketone sensor.

Various other modifications and alterations in the structure and method of operation of this disclosure will be apparent to those skilled in the art without departing from the scope and spirit of the embodiments of the present disclosure. Although the present disclosure has been described in connection with particular embodiments, it should be understood that the present disclosure as claimed should not be unduly limited to such particular embodiments. It is intended that the following claims define the scope of the present disclosure and that structures and methods within the scope of these claims and their equivalents be covered thereby.

What is claimed is:

1. An analyte monitoring system, comprising:
   an on-body unit (OBU) for analyte monitoring, the OBU comprising:
      a transcutaneous analyte sensor;
      electronic circuitry coupled to the analyte sensor; and
      an on-body housing comprising a substantially flat surface and a curved and convex surface opposite the substantially flat surface, wherein the on-body housing has electrical contacts disposed on the curved and convex surface, the electrical contacts electrically coupled to the electronic circuitry; and
   a hand-held reader comprising a plurality of electrical contacts that electrically couple to the electrical contacts on the on-body housing when the reader is positioned in physical contact with the on-body housing.

2. The analyte monitoring system of claim 1, wherein the on-body housing is dome-shaped.

3. The analyte monitoring system of claim 2, wherein electronic circuitry comprises first and second RC pairs in series, and wherein the electrical contacts comprise:
   a first concentric electrical contact electrically connected between the first and second RC pairs;
   a second concentric electrical contact electrically connected to a first end of the first and second RC pairs in series; and
   a third concentric electrical contact electrically connected to a second end of the first and second RC pairs in series;
   wherein the analyte sensor comprises a working electrode and counter electrode, the working electrode coupled to the second concentric electrical contact, and the counter electrode coupled to the third concentric electrical contact.

4. The analyte monitoring system of claim 1, wherein the on-body housing is cone-shaped.

5. The analyte monitoring system of claim 4, wherein the electronic circuitry comprises first and second RC pairs in series, and wherein the electrical contacts comprise:
   a first concentric electrical contact electrically connected between the first and second RC pairs;
   a second concentric electrical contact electrically connected to a first end of the first and second RC pairs in series; and
   a third concentric electrical contact electrically connected to a second end of the first and second RC pairs in series;
   wherein the analyte sensor comprises a working electrode and counter electrode, the working electrode coupled to the second concentric electrical contact, and the counter electrode coupled to the third concentric electrical contact.

6. The analyte monitoring system of claim 1, wherein the electrical contacts comprise first, second, and third concentric electrical contacts disposed on an external surface of the on the on-body housing.

7. The analyte monitoring system of claim 1, wherein the on-body housing comprises a base perimeter with flat edges.

8. The analyte monitoring system of claim 1, wherein the on-body housing comprises a recessed base perimeter.

9. The analyte monitoring system of claim 1, wherein the electronic circuitry comprises first and second RC pairs in series, and wherein the electrical contacts comprise:
   a first concentric electrical contact electrically connected between the first and second RC pairs;
   a second concentric electrical contact electrically connected to a first end of the first and second RC pairs in series; and
   a third concentric electrical contact electrically connected to a second end of the first and second RC pairs in series;
   wherein the analyte sensor comprises a working electrode and counter electrode, the working electrode coupled to the second concentric electrical contact, and the counter electrode coupled to the third concentric electrical contact.

10. The analyte monitoring system of claim 9, wherein the OBU comprises isolated contacts for performing continuity measurements, wherein the isolated contacts are disposed on the on-body housing and isolated from the first and second RC pairs.

11. The analyte monitoring system of claim 10, wherein the first, second, and third concentric electrical contacts are ring-shaped, and wherein the isolated contacts are disposed within all three concentric electrical contacts.

12. The analyte monitoring system of claim 11, wherein each isolated contact is ring-shaped and concentrically disposed.

13. The analyte monitoring system of claim 1, wherein the electronic circuitry is at least partially powered by the analyte sensor.

14. The analyte monitoring system of claim 1, wherein the analyte sensor is a glucose sensor or a ketone sensor.

15. A method, comprising:
   positioning an on-body unit (OBU) on a skin surface, the OBU comprising:
      a transcutaneous analyte sensor;
      electronic circuitry coupled to the analyte sensor; and
      an on-body housing comprising a substantially flat surface and a curved and convex surface opposite the substantially flat surface, wherein the on-body housing has electrical contacts disposed on the curved and convex surface, the electrical contacts electrically coupled to the electronic circuitry;
   physically contacting a hand-held reader to the OBU, wherein the hand-held reader comprises a plurality of electrical contacts that electrically couple to the electrical contacts on the on-body housing when the reader physically contacts the on-body housing; and
   transmitting an analyte sensor signal from the OBU to the reader via the electrical contacts on the on-body housing and the plurality of electrical contacts on the reader, wherein the analyte sensor signal corresponds to an analyte concentration level.

16. The method of claim 15, wherein the on-body housing is dome-shaped.

17. The method of claim 16, wherein the electronic circuitry comprises first and second RC pairs in series, and wherein the electrical contacts comprise:

a first concentric electrical contact electrically connected between the first and second RC pairs;

a second concentric electrical contact electrically connected to a first end of the first and second RC pairs in series; and a third concentric electrical contact electrically connected to a second end of the first and second RC pairs in series;

wherein the analyte sensor comprises a working electrode and counter electrode, the working electrode coupled to the second concentric electrical contact, and the counter electrode coupled to the third concentric electrical contact.

18. The method of claim 15, wherein the on-body housing is cone-shaped.

19. The method of claim 18, wherein the electronic circuitry comprises first and second RC pairs in series, and wherein the electrical contacts comprise:

a first concentric electrical contact electrically connected between the first and second RC pairs;

a second concentric electrical contact electrically connected to a first end of the first and second RC pairs in series; and a third concentric electrical contact electrically connected to a second end of the first and second RC pairs in series;

wherein the analyte sensor comprises a working electrode and counter electrode, the working electrode coupled to the second concentric electrical contact, and the counter electrode coupled to the third concentric electrical contact.

20. The method of claim 15, wherein the electrical contacts comprise first, second, and third concentric electrical contacts disposed on an external surface of the on the on-body housing.

21. The method of claim 15, wherein the on-body housing comprises a base perimeter with flat edges.

22. The method of claim 15, wherein the on-body housing comprises a recessed base perimeter.

23. The method of claim 15, wherein the electronic circuitry comprises first and second RC pairs in series, and wherein the electrical contacts comprise:

a first concentric electrical contact electrically connected between the first and second RC pairs;

a second concentric electrical contact electrically connected to a first end of the first and second RC pairs in series; and a third concentric electrical contact electrically connected to a second end of the first and second RC pairs in series;

wherein the analyte sensor comprises a working electrode and counter electrode, the working electrode coupled to the second concentric electrical contact, and the counter electrode coupled to the third concentric electrical contact.

24. The method of claim 23, wherein the OBU comprises isolated contacts for performing continuity measurements, wherein the isolated contacts are disposed on the on-body housing and isolated from the first and second RC pairs.

25. The method of claim 24, wherein the first, second, and third concentric electrical contacts are ring-shaped, and wherein the isolated contacts are disposed within all three concentric electrical contacts.

26. The method of claim 25, wherein each isolated contact is ring-shaped and concentrically disposed.

27. The method of claim 15, wherein the electronic circuitry is at least partially powered by the analyte sensor.

28. The method of claim 15, wherein the analyte sensor is a glucose sensor or a ketone sensor.

* * * * *